US011938079B2

United States Patent
Liu et al.

(10) Patent No.: US 11,938,079 B2
(45) Date of Patent: Mar. 26, 2024

(54) MASSAGE STICK STRUCTURE

(71) Applicant: BIBOTING INTERNATIONAL CO., LTD, Taoyuan (TW)

(72) Inventors: Po-Chang Liu, Taoyuan (TW); Li-Pin Yuan, Taoyuan (TW)

(73) Assignee: BIBOTING INTERNATIONAL CO., LTD, Taoyuan (TW)

( * ) Notice: Subject to any disclaimer, the term of this patent is extended or adjusted under 35 U.S.C. 154(b) by 586 days.

(21) Appl. No.: 17/146,437

(22) Filed: Jan. 11, 2021

(65) Prior Publication Data

US 2022/0218561 A1     Jul. 14, 2022

(51) Int. Cl.
*A61H 23/00*     (2006.01)
*A61H 9/00*      (2006.01)
*A61H 23/02*     (2006.01)

(52) U.S. Cl.
CPC ......... *A61H 23/004* (2013.01); *A61H 9/0057* (2013.01); *A61H 23/0263* (2013.01); *A61H 2201/0107* (2013.01); *A61H 2201/0157* (2013.01); *A61H 2201/0207* (2013.01); *A61H 2201/0228* (2013.01); *A61H 2201/0278* (2013.01); *A61H 2201/102* (2013.01); *A61H 2201/105* (2013.01); *A61H 2201/1683* (2013.01)

(58) Field of Classification Search
CPC .......... A61H 23/004; A61H 2201/0107; A61H 2201/0157; A61H 2201/0278; A61H 2201/1683; A61H 7/001; A61H 7/008; A61H 23/02; A61H 23/0263; A61H 9/0057; A61H 2201/0153; A61H 2201/0207; A61H 2201/0228; A61H 2201/102; A61H 2201/105; A61H 2201/1215; A61H 2201/168; A61H 2201/5025; A61H 2201/5033; A61H 23/0254; A61H 9/005; A61H 99/00; A61H 39/00; A61H 39/007; A61H 39/06; A61H 2201/10
USPC ......................................................... 601/46
See application file for complete search history.

(56) References Cited

U.S. PATENT DOCUMENTS 5,003,966 A * 4/1991 Saka ...................... A61H 9/005
                                                         601/13
5,454,778 A * 10/1995 Liaskos .................. A61H 9/005
                                                         601/7

(Continued)

FOREIGN PATENT DOCUMENTS

| CN | 106512115 A | * | 3/2017 | |
|---|---|---|---|---|
| CN | 106860928 A | * | 6/2017 | |
| CN | 108309716 A | * | 7/2018 | ............. A61F 7/007 |

*Primary Examiner* — Justine R Yu
*Assistant Examiner* — Benjamin M. Kusiak
(74) *Attorney, Agent, or Firm* — Chun-Ming Shih; HDLS IPR SERVICES

(57) ABSTRACT

A massage stick structure includes a hollow cylinder, a drive control module, and an end cover. The hollow cylinder has a cavity, and a mounting port formed on an end of the hollow cylinder and communicating with the cavity. The drive control module includes a support member, a control assembly and a vibrator fixed to the support member. The end cover is fixed to the support member. The drive control module is disposed into the cavity from the mounting port, and the end cover covers and assembles to the mounting port. Therefore, the assembly process of each component may be simplified to reduce production time and maintenance time.

15 Claims, 9 Drawing Sheets

(56) References Cited

U.S. PATENT DOCUMENTS

| | | | | |
|---|---|---|---|---|
| 6,623,478 B1* | 9/2003 | Hagiwara | A61H 9/005 | 606/7 |
| 11,123,577 B2* | 9/2021 | Blanche | A61H 23/0245 | |
| 2003/0055469 A1* | 3/2003 | Ohmura | A61N 1/44 | 607/109 |
| 2004/0236254 A1* | 11/2004 | Nichols | A61H 7/005 | 601/7 |
| 2005/0070827 A1* | 3/2005 | Lee | A61H 23/0263 | 601/57 |
| 2008/0065176 A1* | 3/2008 | Zhang | A61N 1/44 | 607/88 |
| 2008/0243039 A1* | 10/2008 | Rhoades | A61N 5/0616 | 601/72 |
| 2009/0299234 A1* | 12/2009 | Cho | A61H 9/0057 | 601/2 |
| 2010/0049177 A1* | 2/2010 | Boone, III | A61H 9/0057 | 606/9 |
| 2010/0298745 A1* | 11/2010 | Liu | A61H 9/0057 | 601/12 |
| 2011/0251537 A1* | 10/2011 | Yeo | A61H 7/005 | 601/159 |
| 2011/0319818 A1* | 12/2011 | Shimada | A61F 7/007 | 604/114 |
| 2013/0073017 A1* | 3/2013 | Liu | A61H 39/06 | 607/112 |
| 2014/0221908 A1* | 8/2014 | Sonsino | A61M 3/0283 | 604/35 |
| 2015/0132041 A1* | 5/2015 | Muraki | B01F 33/5011 | 401/4 |
| 2015/0272774 A1* | 10/2015 | Lee | A61H 23/0263 | 601/15 |
| 2016/0001073 A1* | 1/2016 | Ingman | A61N 1/0476 | 607/148 |
| 2016/0051829 A1* | 2/2016 | Porat | A61N 5/062 | 600/26 |
| 2016/0166034 A1* | 6/2016 | Park | A45D 20/08 | 34/96 |
| 2016/0338903 A1* | 11/2016 | Yang | A61H 39/04 | |
| 2018/0185235 A1* | 7/2018 | Nelson | A61H 7/008 | |
| 2019/0029917 A1* | 1/2019 | George | A61H 7/008 | |
| 2019/0111252 A1* | 4/2019 | Kang | A61N 1/328 | |
| 2020/0179220 A1* | 6/2020 | Jablow | A61H 1/00 | |
| 2020/0187986 A1* | 6/2020 | Hsu | A46B 15/0036 | |
| 2020/0222280 A1* | 7/2020 | Jing | A61M 1/08 | |

\* cited by examiner

MASSAGE STICK STRUCTURE

BACKGROUND OF THE INVENTION

1. Technical Field

The technical field of this disclosure relates to a massage stick structure, and particularly relates to an easy-to-assemble massage stick structure.

2. Description of Related Art

Modern people pay more and more attention to maintain physical health with exercise and fitness and various kinds of soreness may occur. A massage stick or a massage chair is often used for massaging and relieving pressure, and the massage stick is used more extensively because of the features of low cost and convenience.

In general, the massage stick is assembled by installing the internal components into a casing first, and then assembling the casing to secure the structure. The related massage stick is difficult to be assembled and the assembling is time-consuming. Further, the non-integrally formed casing may have gaps and poor water resistance. Therefore, how to make the structure of the massage stick easy-to-assemble and have good water resistance is the problem that needs to be solved.

In view of the aforementioned drawbacks of the prior art, the discloser of the present disclosure based on years of experience in the related industry to conduct extensive research and experiment, and finally provided a feasible solution to overcome the drawbacks of the prior art.

SUMMARY OF THE INVENTION

It is a primary object of this disclosure to overcome the drawbacks of the prior art by providing an easy-to-assemble massage stick structure that simplifies the assembly process of each component, so as to reduce production time and maintenance time.

To achieve the aforementioned and other objectives, the present disclosure discloses an easy-to-assemble massage stick structure including a hollow cylinder, a drive control module, and an end cover. The hollow cylinder has a cavity and a mounting port formed on one end of the hollow cylinder and communicating with the cavity. The drive control module includes a support member, and a control assembly and a vibrator fixed to the support member. The end cover is fixed to the support member. The drive control module is disposed into the cavity from the mounting port, and the end cover is assembled to cover the mounting port.

This disclosure has the following functions. The massage stick has better water resistance with the integrally formed hollow cylinder. The upper end cover may be fixed on the opening by the hooks and snap slots. The end cover may be fixed on the mounting port by the fixing holes and locking holes. The hollow convex ring disposed on the bottom of the tray may provide a deep massage effect. The massage stick has the effects of heat compress and medical compress by the heating member and the dressing assembly.

DESCRIPTION OF THE PREFERRED EMBODIMENTS

The technical contents of this disclosure are described with the detailed description of embodiments accompanied with the illustration of related drawings as follows. It is intended that the embodiments and drawings disclosed herein are to be considered illustrative rather than restrictive.

Figure 1:
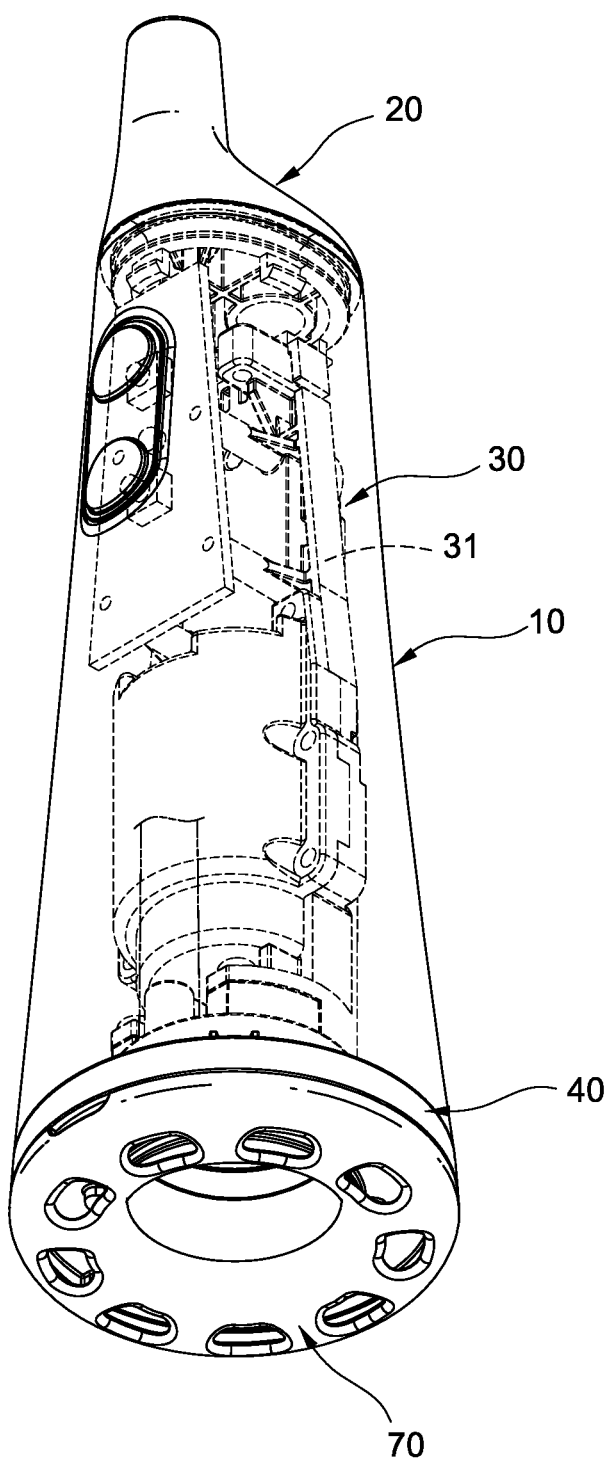
FIG. 1 is a perspective view of a first embodiment of this disclosure.
Figure 2:
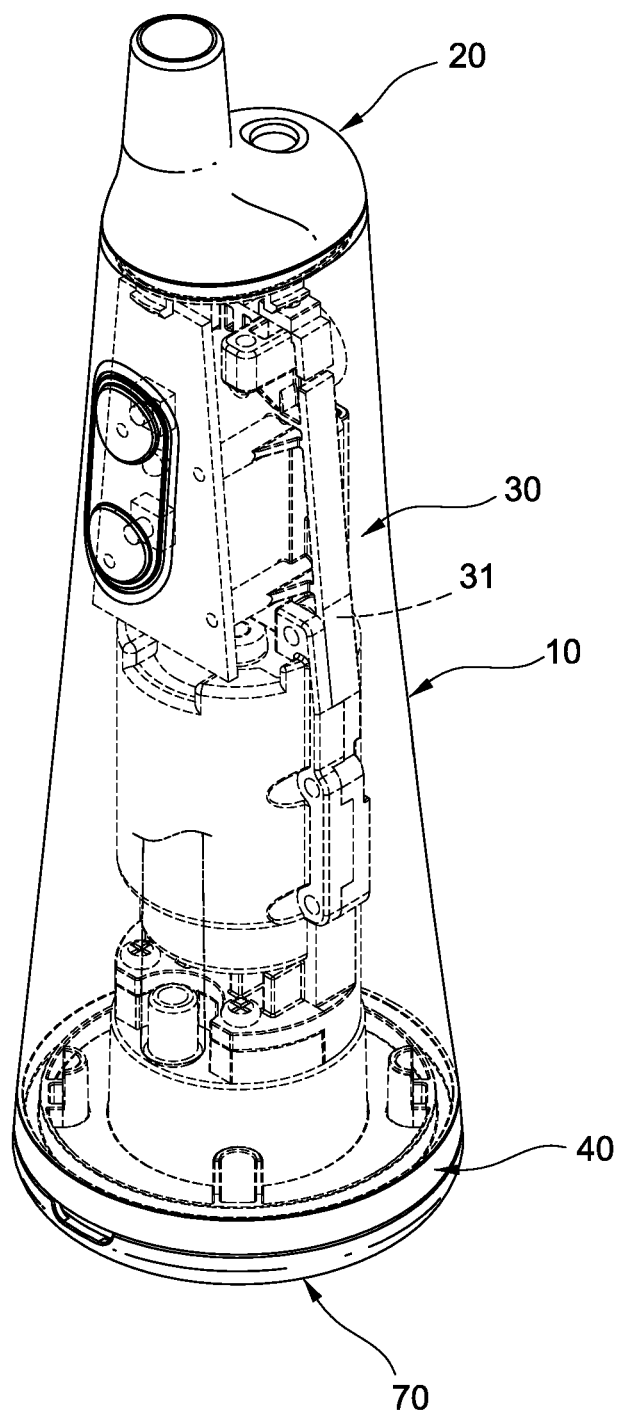
FIG. 2 is another perspective view of the first embodiment of this disclosure.
Figure 7:
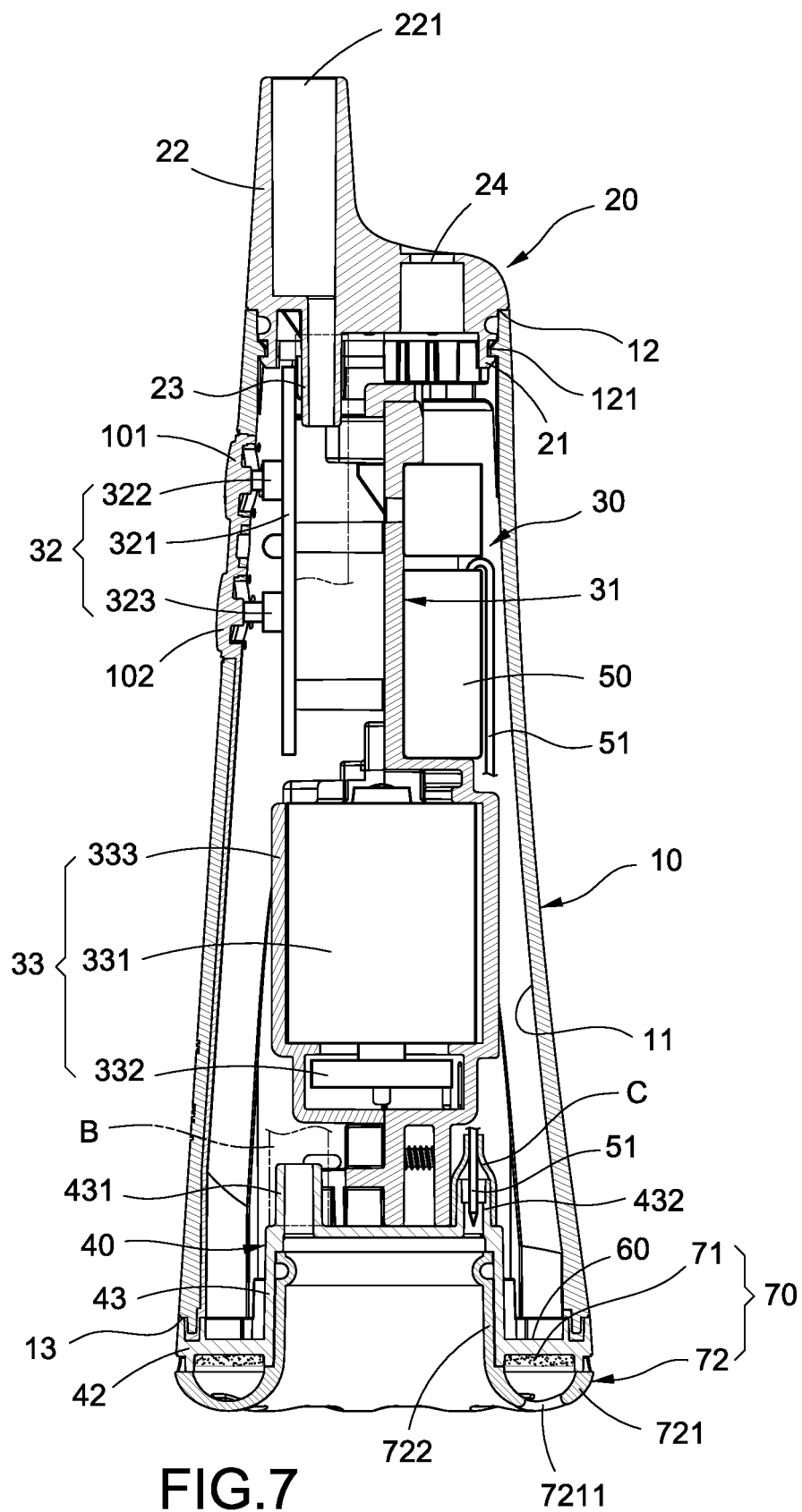
FIG. 7 is a cross-sectional view of the first embodiment of this disclosure.

With reference to FIGS. 1 and 7 for an easy-to-assemble massage stick structure in accordance with the first embodiment of this disclosure, the easy-to-assemble massage stick structure includes a hollow cylinder 10, a drive control module 30 and an end cover 40.

The hollow cylinder 10 is substantially in a conical shape. The hollow cylinder 10 has a cavity 11 and a mounting port 13. The mounting port 13 is formed on one end of the hollow cylinder 10 and communicating with the cavity 11. The drive control module 30 includes a support member 31, a control assembly 32 and a vibrator 33. The control assembly 32 and the vibrator 33 are fixed to the support member 31. The end cover 40 is fixed to the support member 31. The drive control module 30 is disposed into the cavity 11 from the mounting port 13, and the end cover 40 is assembled to cover the mounting port 13.

The massage stick structure of this embodiment further includes an upper end cover 20 and an opening 12. The opening 12 is formed on the other end of the hollow cylinder 10 and communicating with the cavity 11 The upper end cover 20 is assembled to cover the opening 12, and a plurality of hooks 21 are disposed on the bottom of the upper end cap 20, and a plurality of snap slots 121 are disposed on the inner periphery of the opening 12 for engaging the plurality of hooks 21 respectively.

Figure 8:
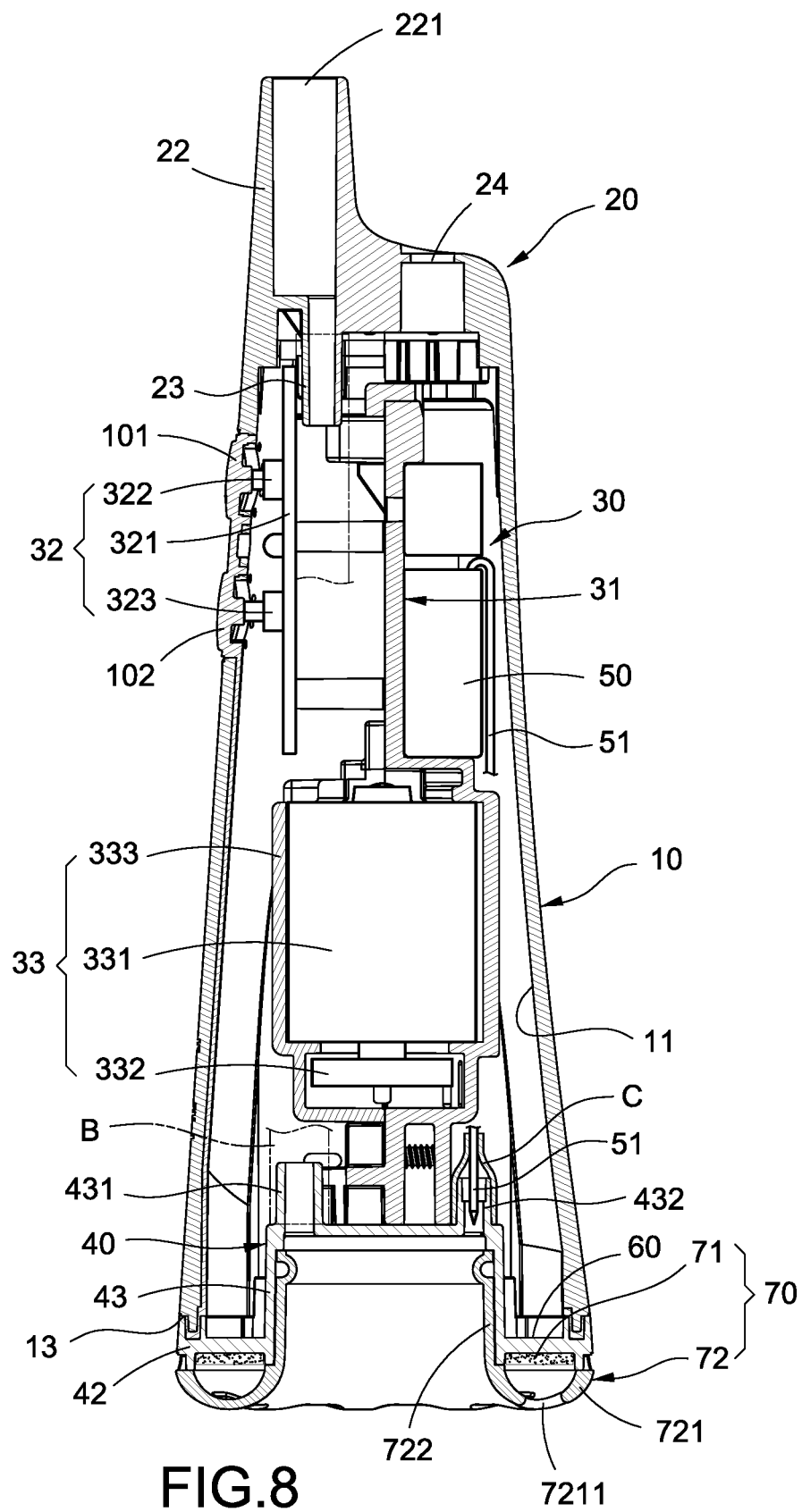
FIG. 8 is a perspective view of a second embodiment of this disclosure.

With reference to FIG. 8 for the second embodiment of this disclosure, the main difference between this embodiment and the previous embodiment is that the upper end cover 20 is formed directly on the other end of the hollow cylinder 10 by injection molding.

With reference to FIGS. 1 to 7, an extension pipe 22 is formed on a side of the upper end cover 20. A negative pressure connection hole 221 is disposed on the center of the extension pipe 22. A first joint pipe 23 is extended under the extension pipe 22. The negative pressure connection hole 221 communicates with the first joint pipe 23. A plurality of hooks 21 are disposed on the bottom of the upper end cover 20. A plurality of snap slots 121 are disposed on the inner periphery of the opening 12 for engaging the plurality of hooks 21 respectively, so that the upper end cover 20 may be fixed to the hollow cylinder 10.

The end cover 40 includes a circular plate 42, a convex base 43 extending from the interior of the circular plate 42. A suction port 44 is disposed on the center of the convex base 43. A second joint pipe 431 extends from a side of the convex base 43 and communicates with the suction port 44. A connecting pipe B is provided for communicating with the first joint pipe 23 and the second joint pipe 431 separately, so that an air transmission channel (not shown in the figure) is formed in the massage stick. The negative pressure connection hole 221 may be connected to an external negative pressure device (not shown in the figure) for inhaling air, so that the suction port 44 produces a negative pressure for massage or the suction port 44 may perform a suction and release massage by a method of alternating a negative pressure relief and negative pressure. A plurality of fixing holes 41 are disposed on the bottom of the end cover 40. A plurality of locking holes 131 are disposed on the mounting port 13. Each fixing hole 41 is provided for a screwing element to pass and fix to each locking hole 131 in order to fix the end cover 40 to the hollow cylinder 10.

Further, the vibrator 33 is installed under the control assembly 32 and electrically coupled to the control assembly 32. The vibrator 33 includes a motor 331, an eccentric member 332 coupled to a shaft of the motor 331 and a fixed cover 333. The eccentric member may be an eccentric wheel or an eccentric block for generating vibrations. The support member 31 has an accommodating slot 311 for accommodating the vibrator 33, and the fixed cover 333 covers the accommodating slot 311 correspondingly. The fixed cover 333 and the support member 31 together enclose the motor 331. A screwing element A is used to fix the fixed cover 333 on the support member 31. The control assembly 32 includes a circuit board 321 and a first switching button 322 installed on the circuit board 321, and a first press button 101 is disposed on the outer periphery of the hollow cylinder 10, the first switching button 322 is disposed corresponding to the first press button 101. The first switching button 322 may be controlled to turn on or turn off the vibrator 33 through pressing the first press button 101.

The massage stick structure of this disclosure further includes an anion generator 50. An embedding slot 312 is disposed on the other side of the accommodating slot 311 of the support member 31, and the anion generator 50 is installed in the embedding slot 312 and electrically coupled to the control assembly 32. By the pulse voltage generated by the anion generator 50, tiny electric arc may be produced to make nearby air generate ozone and anion under the effect of the arc. The anion generator 50 includes an emission needle 51 and a third joint pipe 432. The third joint pipe 432 extends from the other side of the second joint pipe 431 on the convex base 43 and communicates with the suction port 44. The emission needle 51 may communicate with the third joint pipe 432 through a plastic tube C, so that the anion may be discharged by the emission needle 51 from the suction port 44 to outside through the third joint pipe 432. The anion may have regulating effect on autonomic high-level central nervous system, and the functions of improving cerebral cortex, invigorating spirit, relieving fatigue, improving work efficiency and sleep quality.

The massage stick structure of this disclosure further includes a heating member 60 installed in the end cover 40, and the end cover 40 may be made of a metal with preferable thermal conductivity. The heating member 60 of this disclosure is an electric heating plate electrically coupled to the circuit board 321. The control assembly 32 further includes a second switching button 323 installed to the circuit board 321, and a second press button 102 is disposed on the outer periphery of the hollow cylinder, the second switching button 323 is disposed corresponding to the second press button 102. The second switching button 323 may be controlled to turn on or turn off the heating member 60 through pressing the second press button 102. The turned-on heating member 60 may heat up the end cover 40 for massage and warm compress.

Figure 9:
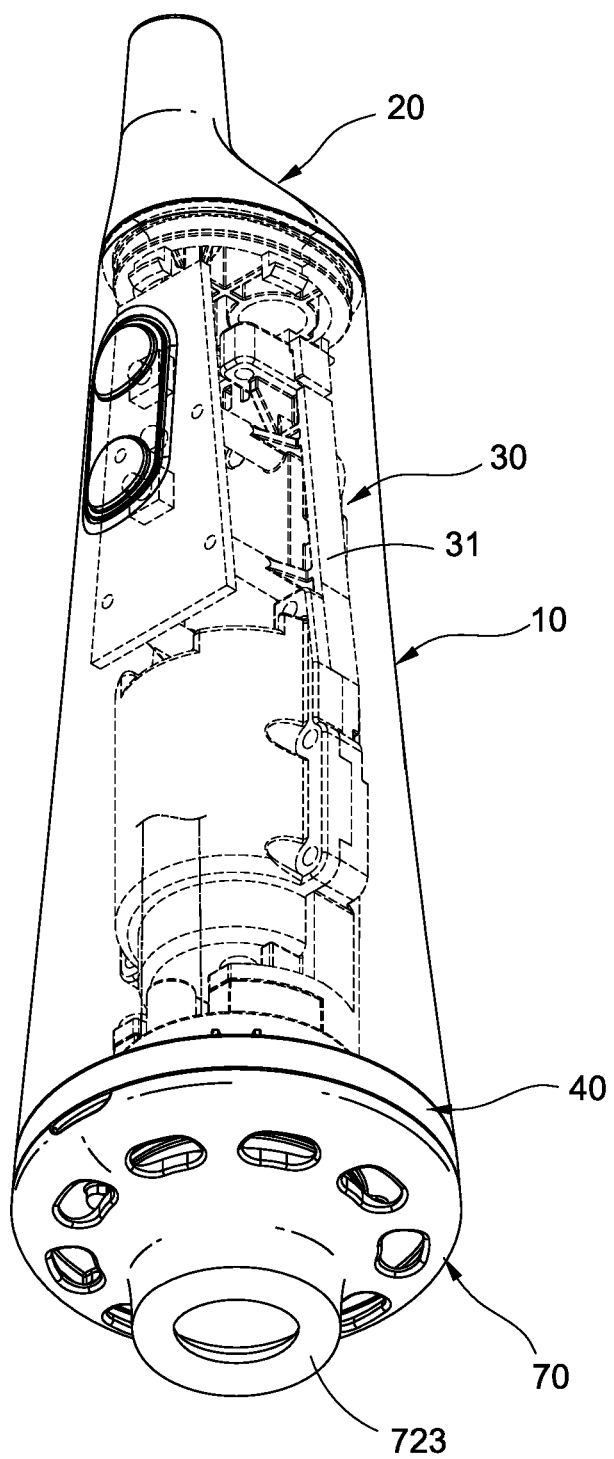
FIG. 9 is a perspective view of a third embodiment of this disclosure.

The massage stick structure of this disclosure further includes a dressing assembly 70 used together with the heating member 60. The dressing assembly 70 is installed corresponding to the bottom of the end cover 40. The dressing assembly 70 includes a medicinal pack 71 and a carrying member 72, and the medicinal pack 71 is formed by packing a traditional Chinese medicine, an herb (such as wormwood), etc. into a packing bag, and the carrying member 72 has a tray 721 placing the medicinal pack 71 and a hollow column 722 extending upwardly from the tray 721. The hollow column 722 passes and connects correspondingly to the suction port 44 and communicates with the suction port 44. A plurality of ventilation holes 7211 are disposed on the tray 721 for volatilization of the medicinal pack 71 after heated. In the third embodiment of this disclosure as shown in FIG. 9, a hollow convex ring 723 protrudes from the bottom of the tray 721 and communicates with the hollow column 722. The hollow convex ring 723 may provide a deep massage effect.

Figure 3:
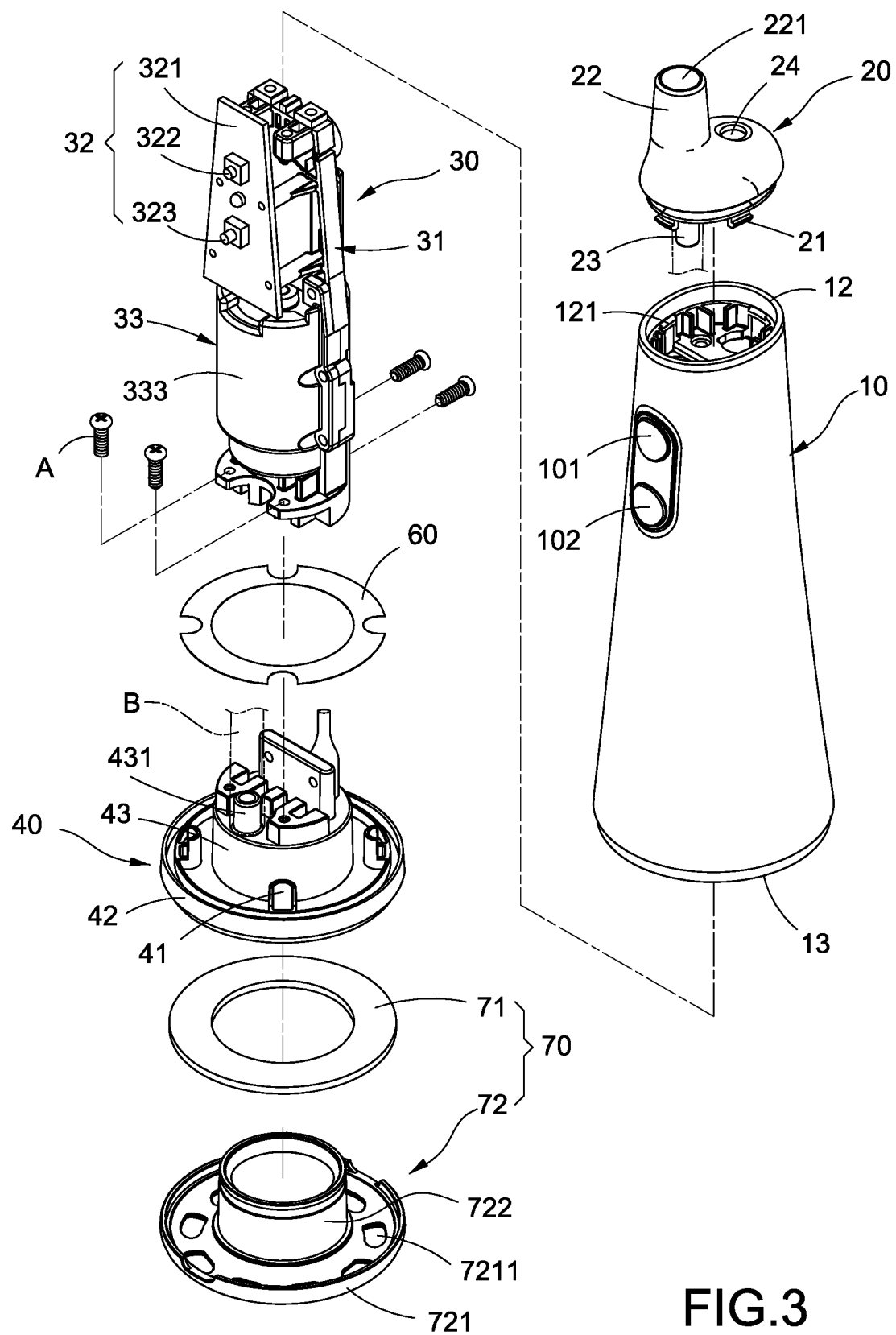
FIG. 3 is an exploded view of the first embodiment of this disclosure.
Figure 4:
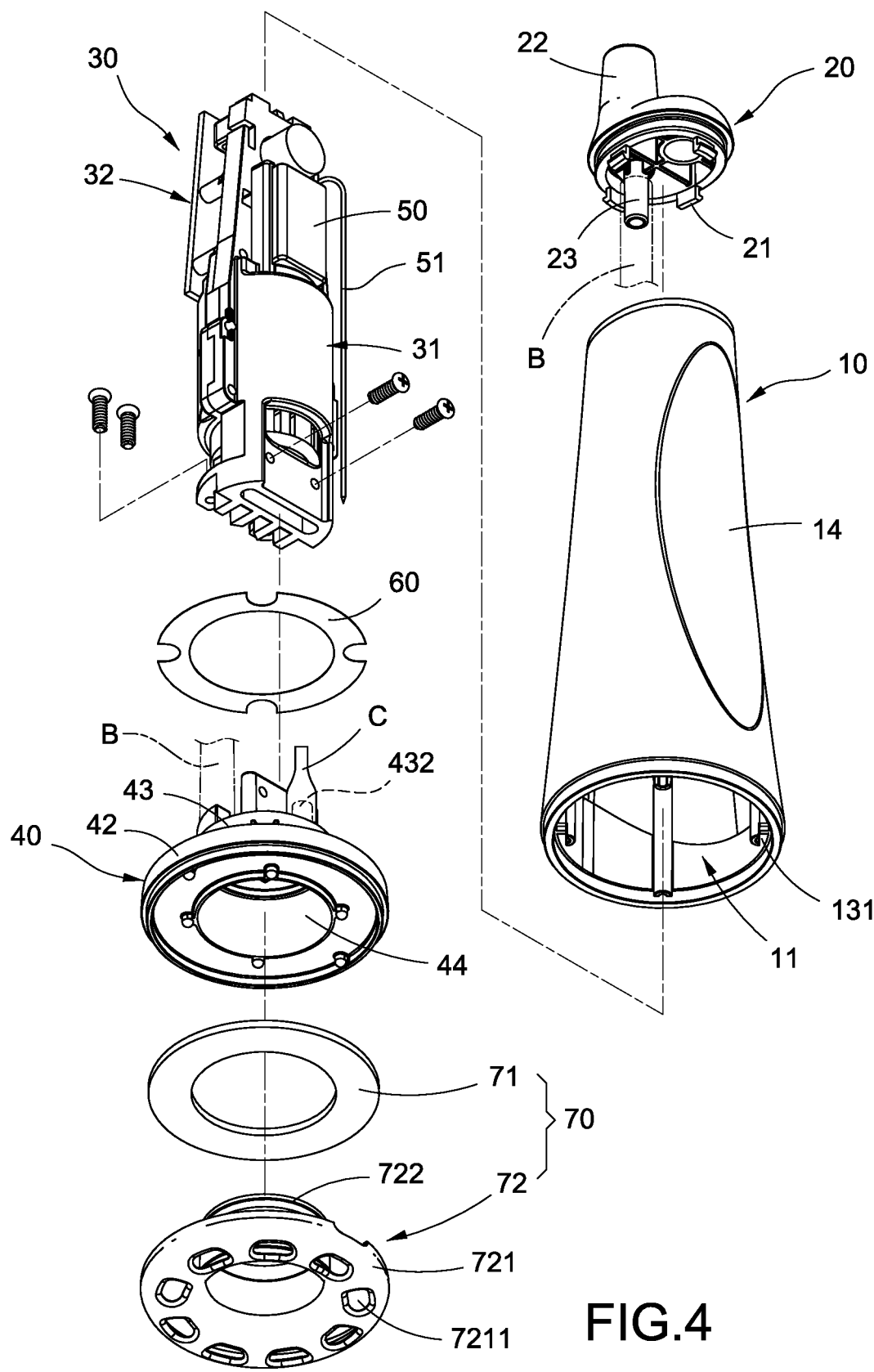
FIG. 4 is another exploded view of the first embodiment of this disclosure.
Figure 5:
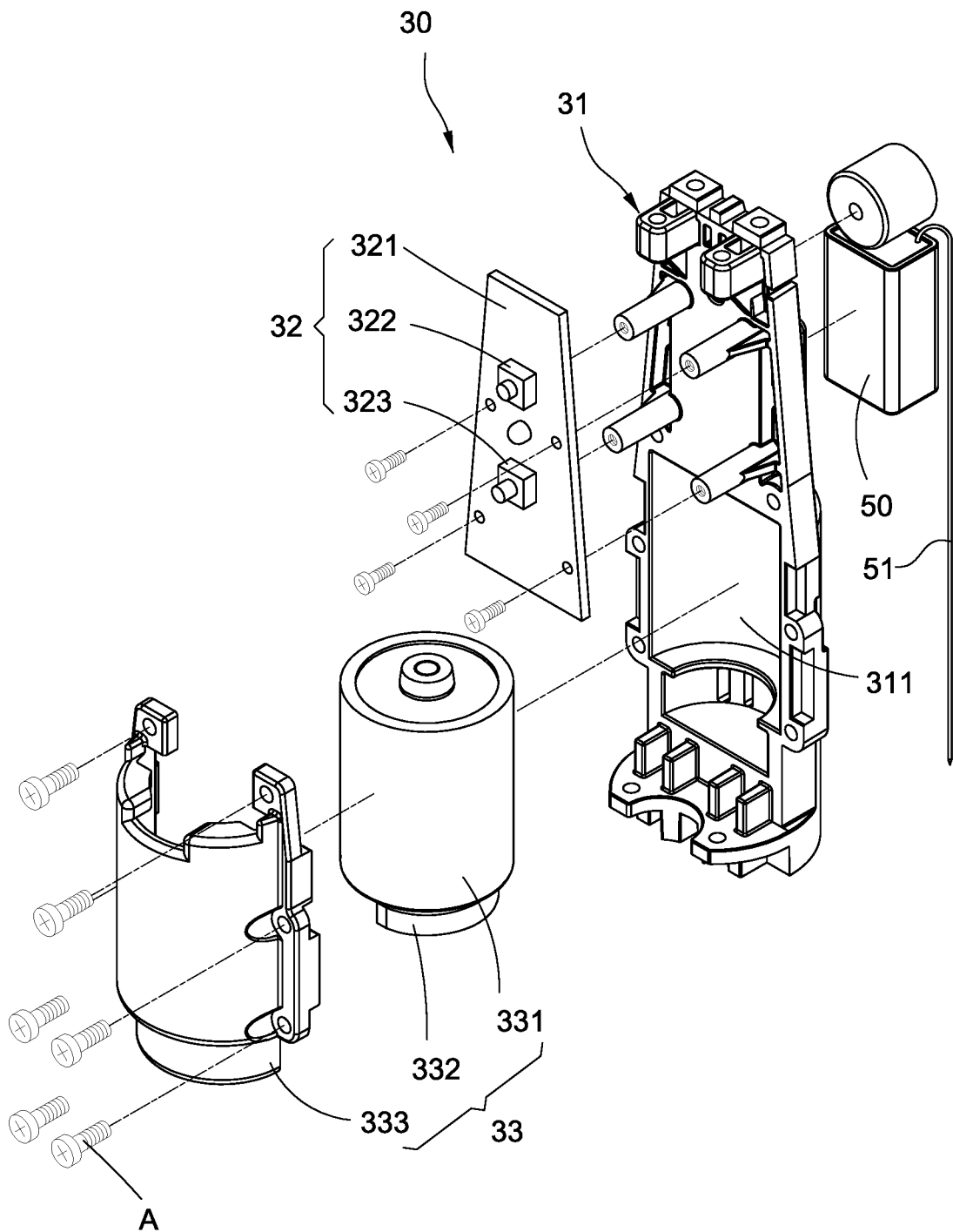
FIG. 5 is an exploded view of a drive control module in accordance with the first embodiment of this disclosure.
Figure 6:
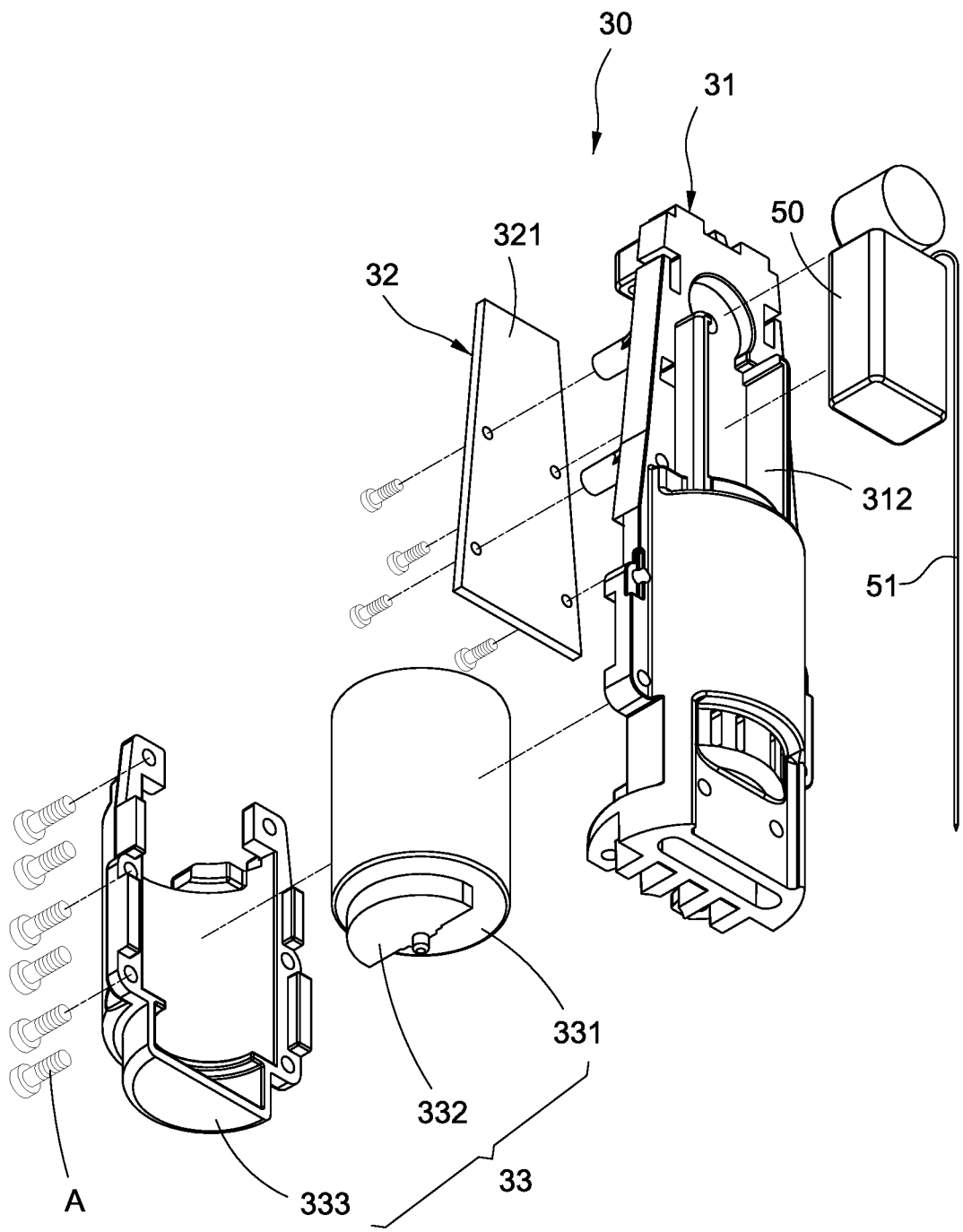
FIG. 6 is another exploded view of a drive control module in accordance with the first embodiment of this disclosure.

In FIG. 3, a connection port 24 is formed on an edge of the extension pipe 22 of the upper end cap 20 and electrically coupled to the control assembly 32. The connection port 24 of this disclosure is a conductive hole. A conductive wire (not shown in the figure) is used to connect other power supply devices (not shown in the figure) for driving the operation of the massage stick. In FIG. 4, the massage stick structure of this disclosure further includes an anti-slip pad 14 adhered on the outer surface of the hollow cylinder 10 to provide the anti-slip and anti-drop effects when holding the massage stick by hand.

With reference to FIGS. 3 to 6 for the assembling procedure of the massage stick structure of this disclosure, the vibrator 33, the control assembly 32 and the anion generator 50 are assembled on the support member 31, and the heating member 60 is installed in the end cover 40 after the drive control module 30 is assembled, and then the end cover 40 is fixed with the assembled drive control module 30. The drive control module 30 is disposed into the cavity 11 of the hollow cylinder 10 from the mounting port 13, and then the end cover 40 is fixed with the hollow cylinder 10, and finally the upper end cover 20 is engaged with the opening 12. The dressing assembly 70 is mounted on the end cover 40 depending on the needs. The assembly of the massage stick structure of this disclosure is thus completed.

While this disclosure has been described by means of specific embodiments, numerous modifications and variations could be made thereto by those skilled in the art without departing from the scope and spirit of this disclosure set forth in the claims.

What is claimed is:

1. A massage stick structure, comprising:
   a hollow cylinder comprising a cavity and a mounting port disposed on one end of the hollow cylinder and communicating with the cavity, wherein the hollow cylinder is in an one-piece form;
   a drive control module comprising a support member, a control assembly, and a vibrator, wherein the control assembly and the vibrator are directly fixed on the support member, and an outer diameter of the drive control module is smaller than an inner diameter of the mounting port;
   an end cover disposed on the mounting port, wherein the support member is directly fixed to the end cover and accommodated in the cavity, and the support member is free from directly contacting the hollow cylinder;

an anion generator installed on the support member and electrically coupled to the control assembly, wherein the end cover comprises a convex base, and the anion generator comprises an emission needle, and an anion joint pipe is extended from a side of the convex base, and the emission needle is coupled to the third joint pipe through a plastic tube.

2. The massage stick structure in claim 1, further comprising: an upper end cover, and an opening disposed on an other end of the hollow cylinder and communicating with the cavity, and the upper end cover being assembled to cover the opening.

3. The massage stick structure in claim 2, wherein the upper end cover comprises a plurality of hooks disposed on a bottom thereof, and a plurality of snap slots are disposed on an inner periphery of the opening, each hook of the plurality of hooks is engaged with a respective snap slot of the plurality of snap slots.

4. The massage stick structure in claim 3, wherein the upper end cover comprises an extension pipe disposed on a side thereof, and the end cover comprises a circular plate, a convex base extending from the circular plate, and a suction port disposed in the convex base.

5. The massage stick structure in claim 4, wherein a first joint pipe is disposed on and extended downward from the extension pipe, a second joint pipe is disposed on and extended from a side of the convex base, and the first joint pipe communicates with the extension pipe, and the second joint pipe communicates with the suction port.

6. The massage stick structure in claim 4, further comprising: a dressing assembly installed on a bottom of the end cover, wherein the dressing assembly comprises a medicinal pack and a carrying member, and the carrying member comprises a tray in which the medicinal pack is placed and a hollow column extending from the tray, and the hollow column coupled to the suction port and communicating with the suction port, and the tray comprises a plurality of ventilation holes for volatilization of the medicinal pack after the medicinal pack is heated.

7. The massage stick structure in claim 6, wherein the carrying member further comprises a hollow convex ring protrudeing from a bottom of the carrying member and communicating with the hollow column.

8. The massage stick structure in claim 1, wherein the hollow cylinder comprises an upper end cover disposed integrally on an other end thereof.

9. The massage stick structure in claim 8, wherein the upper end cover comprises an extension pipe disposed on a side thereof, and the end cover comprises a circular plate, a convex base extending from the circular plate, and a suction port disposed in the convex base.

10. The massage stick structure as claimed in claim 9, wherein a first joint pipe is disposed on and extended downward from the extension pipe, and a second joint pipe is disposed on and extended from a side of the convex base, and the first joint pipe communicates with the extension pipe, and the second joint pipe communicates with the suction port.

11. The massage stick structure in claim 9, further comprising a dressing assembly installed on a bottom of the end cover, wherein the dressing assembly comprises a medicinal pack and a carrying member, and the carrying member comprises a tray in which the medicinal pack is placed and a hollow column extending from the tray, and the hollow column coupled to the suction port and communicating with the suction port, and the tray comprises a plurality of ventilation holes for volatilization of the medicinal pack after the medicinal pack is heated.

12. The massage stick structure in claim 11, wherein the carrying member further comprises a hollow convex ring protruding from a bottom of the carrying member and communicating with the hollow column.

13. The massage stick structure in claim 1, wherein the end cover comprises a plurality of fixing holes disposed on a bottom thereof, and the mounting port comprises a plurality of locking holes, and a screwing element is fixed with each of the locking holes through each of the fixing holes.

14. The massage stick structure in claim 1, wherein the support member comprises an accommodating slot, and the vibrator is installed in the accommodating slot and electrically coupled to the control assembly.

15. The massage stick structure in claim 1, further comprising: a heating member installed in the end cover and electrically coupled to the control assembly.

* * * * *